Feb. 28, 1961 F. MEILLAND Plant Pat. 2,031
ROSE PLANT
Filed June 6, 1960
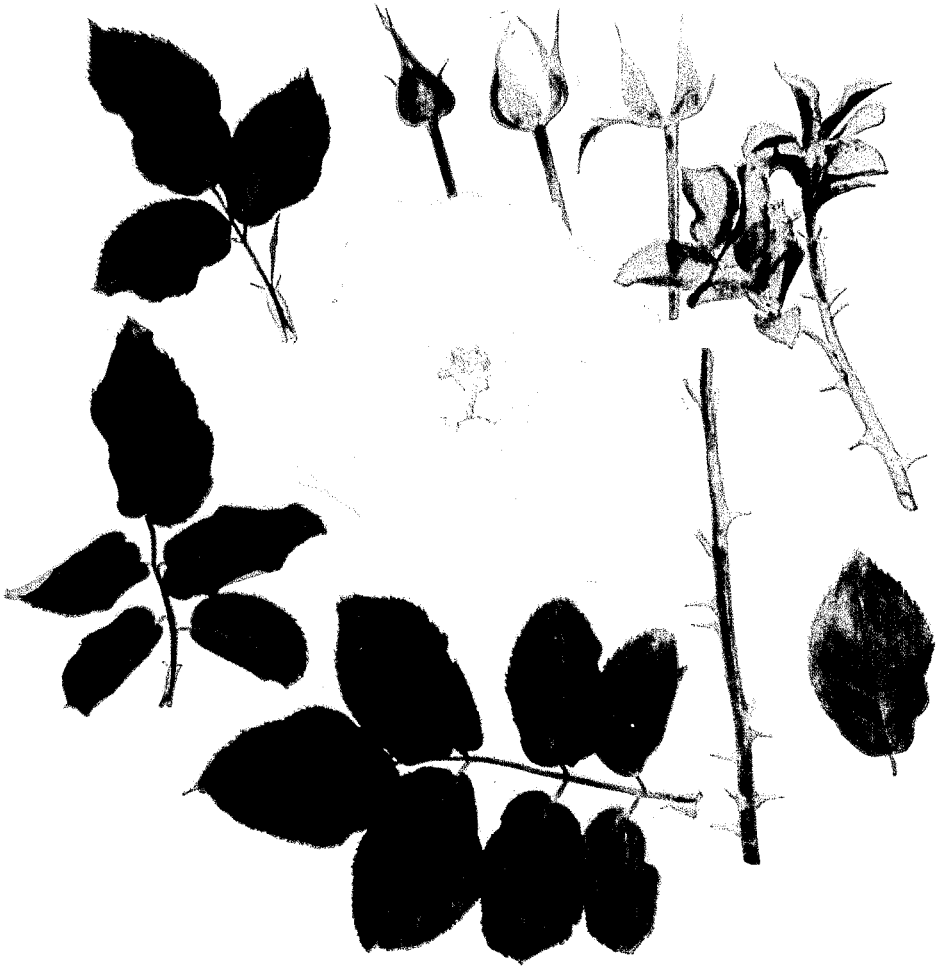
Inventor.
Francis Meilland, Deceased
By: Marie Louise Meilland, née Paolino
Legal Representative
By: Robb & Robb
Attorneys United States Patent Office Plant Pat. 2,031
Patented Feb. 28, 1961

2,031

ROSE PLANT

Francis Meilland, deceased, late of Cap d'Antibes, Alpes Maritimes, France, by Marie Louise Meilland, née Paolino, legal representative, Cap d'Antibes, Alpes Maritimes, France, assignor to The Conard-Pyle Company, West Grove, Pa., a corporation of Pennsylvania Filed June 6, 1960, Ser. No. 34,346

1 Claim. (Cl. 47—61)

The present invention relates to a new and distinct variety of rose plant of the hybrid tea class, which was originated by Francis Meilland, deceased, by crossing the variety "Helene de Roumanie" (unpatented) with the variety "Confidence" (U.S. Plant Patent No. 1,192).

As a result of this breeding, there has been achieved a new and distinct rose variety having the following unique and outstanding combination of characteristics which distinguish the same from the parent varieties, as well as from all other known varieties:

(1) A spreading, well-branched, vigorous habit of growth which is superior to the habit of both parents;

(2) Superior floriferousness as compared with the parent varieties and other varieties in this particular color class;

(3) A superior opening flower form of exhibition type and size; and (4) A distinct varying general color tonality of the flowers, ranging from Peach to Shell-Pink.

Asexual reproduction of the new variety by budding, as performed in France and also at West Grove, Pennsylvania, U.S.A., shows that the foregoing characteristics and distinctions come true to form and are established and transmitted through succeeding propagations.

In comparison with its seed parent "Helene de Roumanie," the new variety has a more uniform and more branched habit of growth, as well as a superior bud form, with the flowers opening more symmetrically, and being of a color which varies from Peach to Shell-Pink as distinguished from the more uniform Coral Pink color of the flowers of this parent. As compared with its pollent parent "Confidence," the new variety has a more spreading habit of growth, but comparable overall vigor; it is more floriferous; the blooms are not as high-centered as those of this parent, and the Shell-Pink color tones of the flowers of the new variety are distinctly lighter than the Cameo Pink color of the flowers of this parent.

The accompanying drawing shows typical specimens of the vegatative growth and flowers of the new variety in different stages of development and as depicted in color as nearly true as it is reasonably possible to make the same in a color illustration of this character.

The following is a detailed description of the new variety, with color terminology in accordance with Horticultural Colour Chart of the Royal Horticultural Society, execpt where general color terms of ordinary dictionary significance are obvious:

Type: Hardy; bush; outdoor; seedling; for garden decoration.

Class: Hybrid tea.

Breeding: Seedling.

*Seed parent.*—"Helene de Roumanie."

*Pollen parent.*—"Confidence."

Propagation: Holds its distinguishing characteristics through succeeding propagations by budding.

*Flower*

Locality where grown and observed: West Grove, Pennsylvania, U.S.A.

Flowers borne: Usually singly to stem; on strong stems of medium length.

Quantity of bloom: Free, outdoors.

Continuity: Continuous.

Fragrance: Moderate. Nature—tea.

Bud:

*Peduncle.*—Medium length; medium heaviness; erect; stiff; entirely smooth. Color—Fern Green, Plate 0862/1.

*Before calyx breaks.*—Size—large. Form—without foliaceous appendages on the surface of the bud; with bristle-like foliaceous parts extending beyond the tip of the bud equal to ¼ or more of its length.

*As calyx breaks.*—Color—near Mars Orange, Plate 013/1.

*As first petal opens.*—Size—large. Form—pointed-ovoid. Color: outside—near Coral Pink, Plate 0619/2, becoming Mimosa Yellow, Plate 602, and veined with Fern Green, Plate 0862/1 over the basal quarter of the petal; inside—between Shell-Pink, Plate 516/3, and Shell-Pink, Plate 516/2 over upper half of the petal, grading to Canary Yellow, Plate 2 over basal half.

*Opening.*—Opens up well.

Bloom:

*Size (when fully open).*—From 4½ inches to 5 inches.

*Petalage.*—Double; from 22 to 38 large petals; arranged regularly.

*Form.*—High-centered at first, but becoming cupped-high centered; petals at first being very loosely rolled outward but later becoming loosely rolled outward at maturity.

Petals:

*Texture.*—Medium soft; with both inside and outside satiny.

*Shape.*—Outer—obovate, with one notch. Intermediate—obovate, with one notch. Inner—obovate; irregular.

This description of a newly opened flower was made from a rose grown outdoors in the month of August at West Grove, Pennsylvania, U.S.A.:

*Color.*—Outer petal: outside surface—near Coral Pink, Plate 0619/3, with base of petal Amber Yellow, Plate 505; inside surface—between Peach, Plate 512/2 and Peach, Plate 512/3, becoming Amber Yellow, Plate 505, with base of petal Canary Yellow, Plate 2. Intermediate petal: outside surface—near Azalea Pink, Plate 618/3, with base of petal Lemon Yellow, Plate 4; inside surface—varying between Peach, Plate 512/2 and Shell-Pink, Plate 516/2 over upper half of petal; grading to Straw Yellow, Plate 604/1, with base of petal Canary Yellow, Plate 2. Inner petal: outside surface—near Azalea Pink, Plate 618/3, grading to Straw Yellow, Plate 604/1 over base quarter, with base of petal Lemon Yellow, Plate 4; inside surface—varying between Peach, Plate 512/2 and Shell-Pink, Plate 516/2, at apical margin, becoming Straw Yellow, Plate 604/1 over main body of petal, with basal quarter Canary Yellow, Plate 2.

This description was made from a rose that was open for three days outdoors in the month of August at West Grove, Pennsylvania, U.S.A.:

*Color.*—Outer petal; outside surface—near Coral Pink, Plate 0619/3, grading to Chinese Yellow, Plate 606/2, with base of petal Mimosa Yellow, Plate 602/1; inside surface—outer margin of petal varying between Peach, Plate 512/2 and Shell-Pink, Plate 516/2, bordering Chinese Yellow, Plate 606/2, with base of petal Canary Yellow, Plate 2. Inner petal: outside surface—near Coral Pink, Plate 0619/3, grading to Chinese Yellow, Plate 606/2, with base of petal Mimosa Yellow, Plate 602/1; inside surface—apical half of petal varying between Peach, Plate 512/2 and Shell-Pink, Plate 516/2, grading to Chinese Yellow, Plate 606/2, with base of petal Canary Yellow, Plate 2.

*General color effect.*—Newly opened flower—near Peach, Plate 512/2, bordering Straw Yellow, Plate 604/1. 3-days open—between Shell-Pink, Plate 516/2 and Shell-Pink, Plate 516/3.

*Behavior.*—Drop off cleanly; opened petals weather-mark easily during cold, hot and wet weather.

*Flower longevity.*—On bush in garden—3 days in August. Cut roses grown outdoors and kept at living-room temperatures—3 days in August.

*Reproductive organs*

Stamens: Medium number; arranged regularly about pistils; mixed with petaloids.

Filaments: Most with anthers; medium length. Color—Vermilion, Plate 18/1, grading to Tangerine Orange, Plate 9/1 at tip.

Anthers: All open at once; large; seldom an anther fused with a petaloid. Color—Barium Yellow, Plate 503/1.

Pollen: Moderate abundance. Color—Lemon Yellow, Plate 4.

Pistils: Medium number.

Styles: Uneven; medium length; medium caliper; loosely bunched.

Stigma: Color—yellow.

Ovaries: All protruding from receptacle.

Hips: None observed.

Sepals: Permanent; moderately long; spear-shaped.

Seeds: None observed.

*Plant*

Foliage:

*Leaves.*—Compound of usually 5 leaflets; abundant; medium size; leathery.

*Leaflets.*—Shape—oval, with apex acute. Base—obtuse.—Margin—simply serrate.

*Color.*—Mature: upper surface—Spinach Green, Plate 0960; under surface—Lavender Green, Plate 000761/1. Young: upper surface—Fern Green, Plate 0862, overlaid with Oxblood Red, Plate 00823/3; under surface—Fern Green, Plate 0862, heavily overlaid with Oxblood Red, Plate 00823/3.

*Rachis (the supporting stem of the compound leaf).*—Medium caliper. Upper side—grooved; hairy. Under side—smooth.

*Stipules.*—Moderately long; moderately wide; with short points turning out at an angle of 45°.

*Disease resistance.*—Comparable to that of the average variety grown under the same cultural conditions at West Grove, Pennsylvania, U.S.A.

Growth:

*Habit*—Bushy; upright; much-branched.

*Growth.*—Free.

*Canes.*—Medium heavy.

*Main stems.*—Dull. Color—near Spinach Green, Plate 0960/2. Prickles—Several; color—near Garnet Brown, Plate 00918/3. Hairs—none.

*Branches.*—Dull. Color—near Spinach Green, Plate 0960/2. Prickles—several; color—near Fern Green, Plate 0862/3, very lightly overlaid at the base with Garnet Brown, Plate 00918/3. Hairs—none.

*New shoots.*—Bright. Color—near Lettuce Green, Plate 861. Prickles—several; color—near Fern Green, Plate 0862/3, overlaid at the base with Garnet Brown, Plate 00918/3. Hairs—none.

What is claimed is:

A new and distinct variety of rose plant of the hybrid tea class, substantially as herein shown and described, characterized particularly as to novelty by the unique combination of a spreading, well-branched, vigorous habit of growth, superior floriferousness in comparison with other varieties of its color class, a superior opening flower form of exhibition type and size, and a distinctive, varying general color tonality of the flowers ranging from Peach to Shell-Pink.

No references cited.